(12) United States Patent
Auguste et al.

(10) Patent No.: US 6,375,977 B1
(45) Date of Patent: Apr. 23, 2002

(54) HYDROCOLLOID ADHESIVE MASS USEFUL FOR MEDICAL PURPOSES

(75) Inventors: Stephane Auguste, Quetigny; Laurent Apert; Luc Garima, both of Dijon, all of (FR)

(73) Assignee: Laboratoires d'Hygiene et de Dietetique, Chenove (FR)

( * ) Notice: Subject to any disclaimer, the term of this patent is extended or adjusted under 35 U.S.C. 154(b) by 0 days.

(21) Appl. No.: 09/655,429

(22) Filed: Sep. 5, 2000

Related U.S. Application Data

(63) Continuation of application No. PCT/FR99/00553, filed on Mar. 12, 1999.

(51) Int. Cl.[7] .......................... A61L 15/16; A61L 15/00; A61F 13/02; A61K 13/74
(52) U.S. Cl. ........................ 424/447; 424/445; 424/448; 424/78.06
(58) Field of Search ................................ 424/400, 443, 424/444, 445, 446, 447, 448, 449, 78.06

(56) References Cited

U.S. PATENT DOCUMENTS

| 5,429,590 A | 7/1995 | Saito et al. ................ 602/48 |
| 5,456,745 A | 10/1995 | Roreger et al. ............ 106/128 |
| 5,750,134 A | 5/1998 | Scholz et al. .............. 424/434 |
| 5,750,136 A | 5/1998 | Scholz et al. .............. 424/448 |
| 6,051,748 A | * 4/2000 | Auguste et al. ............. 602/54 |
| 6,139,866 A | * 10/2000 | Chono et al. ............... 424/443 |

FOREIGN PATENT DOCUMENTS

| EP | 0 355 536 A | 2/1990 |
| EP | 601 463 A1 | 6/1994 |
| WO | WO 91 06290 A | 5/1991 |

* cited by examiner

Primary Examiner—Gollamudi S. Kishore
Assistant Examiner—Todd D Ware
(74) Attorney, Agent, or Firm—Pennie & Edmonds LLP

(57) ABSTRACT

The present invention relates to a novel hydrocolloid adhesive mass useful for medical purposes, characterized in that said hydrocolloid adhesive mass comprises:

a) 0.2 to 5 parts by weight of an ethoxylated sorbitan fatty acid ester;
b) 20 to 50 parts by weight of a hydrocolloid;
c) 32 to 120 to parts by weight of an adhesive matrix made up of one or more polymers selected from poly(styrene/olefin/styrene) block copolymers, low-molecular polyisobutylenes and high-molecular polyisobutylenes, and one or more compounds selected from sticky resins, or tackifying resins, plasticizers, polybutenes, antioxidants, ethylene/vinyl acetate copolymers, butyl rubbers and ethylene/propylene block copolymers; and
d) 0 to 15 parts by weight of an acrylate copolymer with a glass transition temperature below −20° C. It further relates to the use of this hydrocolloid adhesive mass for the production of dressings, especially for the treatment of superficial, deep, chronic or acute dermo-epidermal lesions, exudative wounds and bums.

35 Claims, No Drawings

HYDROCOLLOID ADHESIVE MASS USEFUL FOR MEDICAL PURPOSES

This application is a continuation of PCT/FR99/0053 filed Mar. 12, 1999.

FIELD OF THE INVENTION

The present invention relates to novel hydrocolloid adhesive masses with increased absorption in the first few hours of use.

The invention further relates to the use of these novel hydrocolloid adhesive masses for medical purposes in dermatology or cosmetology, particularly for the production of dressings for the treatment of blisters, exudative wounds, burns and superficial, deep, chronic or acute dermo-epidermal lesions.

The treatment of superficial, deep, chronic or acute dermo-epidermal lesions, burns and, in particular, exudative wounds is a complex problem to which the dressings developed: in recent years have not provided totally satisfactory solutions.

The loss of substances caused by a mechanical compression which creates tissue ischemia, or by problems of vascular origin (irrigation, pressure, etc.), an injury (ablation of tissue,: flesh, etc.), an abscess or a burn, is generally referred to as the exudation of a wound. The phenomenon of exudation corresponds to excretion of the biological fluids produced by the wound throughout the healing process.

Exudation originates from the blood and is controlled by the mediators of the inflammatory reaction (vasodilation and vasoconstriction) with passage of these fluids through the vascular membranes. These fluids then flood the bed of the wound and constitute the factors which favor degradation of the perilesional healthy tissues, accompanied in particular by maceration phenomena and risks of superinfection.

The role of a dressing is to absorb these fluids while at the same time maintaining in contact with the wound a moist environment which favors the healing processes.

The ideal dressing must therefore be capable of absorbing these exudates throughout the healing of the wound.

Depending on the severity of the wound, this. healing process may extend from a few days, for wounds producing very little exudation, to several months. This involves changing the dressing frequently in order to maintain its absorption capacity and its efficacy.

To minimize the number of changes of dressing, which are traumatizing for the patient and for the healing quality (pulling-away of neoformed tissues, bleeding, pain, etc.), so-called "hydrocolloid" dressings based on hydrocolloid adhesive masses are now used to maintain an absorption capacity over 2 to 4 days.

These hydrocolloid adhesive masses, also described as hydrophilic adhesive masses, are formed mainly of an adhesive matrix, generally consisting of at least one elastomer selected from polymers such as polyisobutylenes or poly(styrene/olefin/styrene) block copolymers, which may or may not be associated with adhesion improvers such as sticky resins, or tackifying resins, plasticizers such as polybutenes or plasticizing oils, or cohesion improvers such as butyl rubbers, etc., and of one or more hydrocolloids.

Numerous hydrocolloid adhesive masses employed in the production of such dressings have already been described. Examples which may thus be mentioned are patent US:3 972 328 and the following patent applications: FR-A-2 495 473, EP-A-130 061 and EP-A-302 536.

However, none of these documents tackles another important aspect of exudation, namely its kinetic aspect over time.

It is in fact known that the phenomenon of exudation is always more important at the start of the healing process, which corresponds to the critical phase of the inflammatory reaction. This inflammatory reaction is most important during the first 4 hours, so it is a matter of urgency to re-establish the hemostatic equilibrium of the wound, i.e. to increase the absorption capacity during the first few hours. In fact, the more rapidly this equilibrium is reached, the less the wound will weep and the better the absorption capacity of the dressing will be maintained at a high level over several days. It will thus be possible to make the changes of dressing less frequent and avoid the associated disadvantages already mentioned.

Likewise, each time the dressing is changed when the wound is tended, cleaned and disinfected, and before a new dressing is applied, the wound is faced with a more aggressive environment (contact with the air, loss of moisture, etc.). This causes a resumption of the inflammatory reaction, which will induce an increase in the exudates produced, so there is again a need in this case to increase the absorption capacity during the first few hours.

An ideal dressing should therefore be adapted to the amount of exudates produced, but also to theirate of production.

To adapt the absorption capacity to the rate of production, one might consider increasing the amount of hydrocolloid which gives these adhesive masses their absorption property. However, if too much of this type of product is incorporated into the adhesive mass, said products will swell proportionately to their concentration and will degrade the physical properties of the dressing, resulting in a loss of cohesion and meaning that the dressing falls apart when removed or may even be wasted. Consequently, this solution cannot be satisfactory because this situation once again raises the problems associated with changing of the dressing and with the life of the dressing.

OBJECTS OF THE INVENTION

Under these conditions, the object of the present invention is to solve the new technical problem consisting in the provision of a hydrocolloid adhesive mass of novel composition which has a high absorption as from the first few hours without impairment of its properties of cohesion, adhesion and manageability in the medium and long term.

SUBJECTS OF THE INVENTION

It has been discovered that it is possible to solve this technical problem in an entirely satisfactory manner, which is simple to implement, by incorporating an ethoxylated sorbitan fatty acid ester, preferably a monoester, into a traditional hydrocolloid adhesive mass. It is this discovery which constitutes the basis of the present invention.

Furthermore, it has been found that the addition of an ethoxylated sorbitan fatty acid ester to a traditional hydrocolloid adhesive mass, particularly an adhesive mass comprising an elastomer of the poly(styrene/isoprene/styrene) type, affords a significant increase in the capacity of said mass to discharge the absorbed fluids by increasing the permeability to water vapor. Thus the novel hydrocolloid masses according to the invention can be used to produce dressings which are capable of eliminating the absorbed fluids and, consequently, of maintaining an absorption-elimination equilibrium and a moist environment favorable to healing.

Thus, according to a first feature, the present invention relates in general terms to a hydrocolloid adhesive mass consisting of a hydrocolloid and an adhesive matrix, with which an acrylate polymer with a glass transition temperature below −20° C. may or may not be associated, and of an ethoxylated fatty acid ester.

More precisely, the present invention relates to a hydrocolloid adhesive mass useful especially for medical purposes, characterized in that said hydrocolloid adhesive mass comprises:

(a) 0.2 to 5 parts by weight of an ethoxylated sorbitan fatty acid ester;

(b) 20 to 50 parts by weight of a hydrocolloid;

(c) 32 to 120 parts by weight of an adhesive matrix made up of one or more polymers selected from poly(styrene/olefin/styrene) block copolymers, low-molecular polyisobutylenes and high-molecular polyisobutylenes, and one or more compounds selected from sticky resins, or tackifying resins, plasticizers, polybutenes, antioxidants, ethylene/vinyl acetate copolymers, butyl rubbers and ethylene/propylene block copolymers; and (d) 0 to 15 parts by weight of an acrylate polymer with a glass transition temperature below −20° C.

Ethoxylated sorbitan fatty acid ester is understood here as denoting ethoxylated sorbitan fatty acid esters (especially monoesters, triesters or mixtures thereof) in which each fatty acid part of the ester contains from 8 to 22 carbon atoms and is a linear or branched chain, preferably a linear chain, which is saturated or possesses one or more sites of olefinic unsaturation.

Within the framework of the present invention, particularly preferred ethoxylated sorbitan fatty acid esters will be those referred to as polysorbates and corresponding to the ethoxylated sorbitan fatty acid monoesters and triesters respectively represented by formulae I and II below, in which the sum w+x+y+z can take the value 20, 5 or 4 and R is the hydrocarbon part of the fatty acid containing from 7 to 21 carbon atoms.

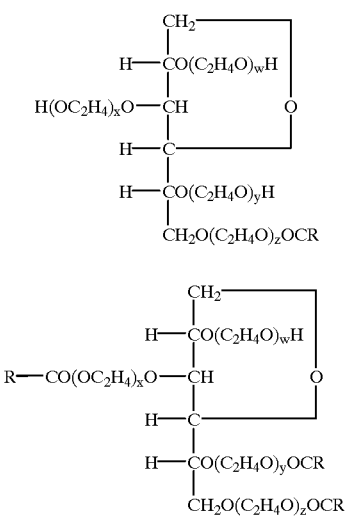

Thus preferred ethoxylated sorbitan monoesters of formula I will be those for which the sum w+x+y+z=20, for example ethoxylated sorbitan monolaurate (also called polysorbate 20), ethoxylated sorbitan monopalmitate (also called polysorbate 40), ethoxylated sorbitan monostearate (also called polysorbate 60), ethoxylated sorbitan monooleate (also called polysorbate 80) and ethoxylated sorbitan monoisostearate (also called polysorbate 120). Preferred monoesters of formula I for which w+x+y+z=4 will be ethoxylated sorbitan monolaurate (also called polysorbate 21) and ethoxylated sorbitan monostearate (also called polysorbate 61). Finally, the preferred monoester of formula I for which w+x+y+z=5 will be ethoxylated sorbitan monooleate (also called polysorbate 81).

Likewise, preferred ethoxylated sorbitan triesters of formula II will be those for which the sum w+x+y+z=20, for example ethoxylated sorbitan tristearate (also called polysorbate 65) and ethoxylated sorbitan trioleate (also called polysorbate 85).

Within the framework of the present invention, polysorbate 80 will be very particularly preferred, examples being the products marketed by SEPPIC under the names MONTANOX® 80 and MONTANOX® 80VG (which has an identical composition to the first product except that in this case the fatty acid part is of vegetable origin).

According to a second feature, the present invention relates to the use of these hydrocolloid adhesive masses for the production of dressings especially for the treatment of blisters, superficial, deep, chronic or acute dermo-epidermal lesions, exudative wounds and burns.

The adhesive matrices which can be used in the production of the hydrocolloid adhesive masses are the ones commonly employed by those skilled in the art. They are formed of at least one elastomer selected from polymers such as polyisobutylenes or poly(styrene/olefin/styrene) block copolymers, for example poly(styrene/isoprene/styrene), poly(styrene/butadiene/styrene) or poly(styrene/ethylene/butylene/styrene), which may or may not be associated with antioxidants, adhesion improvers such as sticky resins, or "tackifying" resins, plasticizers such as polybutenes or plasticizing oils, or cohesion improvers such as butyl rubbers, etc.

Such compositions are thus defined in chapter 7, "Wound Dressings", pages 158 to 171, of "Advances in Pressure Sensitive Adhesive Technology-2", published in April 95 by Donatas Satas.

Reference may also be made in this respect to the prior art documents mentioned above for the definitions of all the compounds used in these formulations and their respective proportions in the adhesive matrix.

Thus, in the case of an adhesive matrix based on polyisobutylene elastomer, polyisobutylenes with a low molecular weight of the order of 40,000 to 80,000 daltons will be used, such as the compounds marketed under the name VISTANEX® by EXXON CHEMICAL or under the name OPPANOL® by BASF.

The products marketed under the names VISTANEX® LM-MS, VISTANEX® LM-MH, OPPANOL® B12 and OPPANOL® B15 will be particularly preferred.

The latter products may be used by themselves or in a mixture.

If necessary, these polyisobutylenes may be associated with additional compounds for improving the properties of elasticity, strength or cohesion, such as polyisobutylenes with a high molecular weight of the order of 400,000 to 2,000,000 daltons, for example the: products marketed by EXXON CHEMICAL under the names VISTANEX® L-80 or VISTANEX® L-100, ethylene/vinyl acetate copolymers, for example those marketed under the name ELVAX® by DUPONT or under the names ULTRATHENE® and VYNATHENE® by U.S.I. Chemicals, ethylene/propylene block copolymers, for example those marketed by DUPONT under the name NORDEL®, or butyl rubbers, for example those marketed under the names GRADE® 065 or GRADE® 067 by EXXON CHEMICAL.

Plasticizers such as polybutenes, for example those marketed by BP CHEMICALS under the. name NAPVIS® 10, can also be incorporated into these adhesive matrices.

Such adhesive matrices will be formulated in conventional manner by those skilled in the art to give the desired adhesive and mechanical properties by adapting the amount of each compound.

Block copolymers of the poly(styrene/olefin/styrene) type may likewise be added to these adhesive matrices based on polyisobutylenes. In that case it will be preferable to use poly(styrene/isoprene/styrene) copolymers, for example the products marketed under the names KRATON® D-1107 or KRATON® 1161 by SHELL CHEMICALS or the product marketed under the name VECTOR® 4113 by EXXON CHEMICAL, or poly(styrene/butadiene/styrene) copolymers, for example the product marketed under the name KRATON® D-1102 by SHELL CHEMICALS.

Such formulations of adhesive matrices are described for example in patent application EP-A-130 061.

Similarly, it will be possible to use adhesive matrices based solely on an elastomer of the poly(styrene/olefin/styrene) block copolymer type, particularly those based on poly(styrene/isoprene/styrene) or poly(styrene/ethyleneibutylene/styrene), which are associated with plasticizers, "tackifying" resins, antioxidants, etc. to give the desired adhesive and cohesive properties.

Such formulations of adhesive matrices are also perfectly familiar to those skilled in the art.

The block copolymers of the styrene/olefin/styrene type which can be used within the framework of the preparation of these adhesive matrices are the ones normally used by those skilled in the art, and reference may be made in this respect to the prior art document mentioned above.

The olefin blocks of these copolymers can consist of isoprene, butadiene, ethylene/butylene or ethylene/propylene units and mixtures thereof.

Within the framework of the present invention, poly (styrene/isoprene/styrene) three-block copolymers are preferred.

Three-block copolymer of the poly(styrene/isoprene/styrene) type [abbreviated to poly(SIS)] is understood here as meaning a poly(SIS) material with a styrene content of between 14 and 52% by weight, based on the weight of said poly(SIS). This expression also covers poly(SIS) materials containing a mixture of poly(SIS) three-block copolymers and two-block copolymers of the poly(styrene/isoprene) type.

Such products, which are well known to those skilled in the art, are marketed for example by SHELL and EXXON CHEMICAL under the names KRATON® D and VECTOR® respectively.

Within the framework of the present invention, three-block copolymers with a styrene content of between 14 and 30% by weight, based on the weight of said poly(SIS), are preferred. The products marketed by EXXON CHEMICAL and SHELL CHEMICALS under the respective names VECTOR® 4114 and KRATON® D-1111CS will be particularly preferred.

Among the tackifying resins suitable for the production of these adhesive matrices, there may be mentioned the resins generally employed in the field of adhesives by those skilled in the art, such as modified polyterpene or terpene resins, hydrogenated rosin resins, polymerized rosin resins, rosin ester resins, hydrocarbon resins, mixtures of aromatic and aliphatic resins, etc. A synthetic resin formed of $C_5/C_9$ copolymers and marketed by GOOD YEAR under the name WINGTACK® 86 will be particularly preferred within the framework of the present invention.

Antioxidants are understood here as denoting the compounds commonly employed by those skilled in the art for ensuring that the compounds used in the formulation of the matrices, particularly the tackifying resins and the block copolymers, are stable towards oxygen, heat, ozone and ultraviolet radiation. It is possible to use one or more of these antioxidants in association.

Appropriate antioxidants which may be mentioned are phenolic antioxidants, for example the products marketed by CIBA-GEIGY under the names IRGANOX® 1010, IRGANOX® 565 and IRGANOX® 1076, and sulfur-containing antioxidants, for example the zinc dibutyldithiocarbamate marketed by AKZO under the name PERKACIT® ZDBC.

The association of IRGANOX® 1010 and PERKACIT® ZDBC will be preferred within the framework of the present invention.

Any type of plasticizer normally used by those skilled in the art for the preparation of an adhesive matrix based on styrene/olefin/styrene block copolymer can be used within the framework of the present invention, although it will be preferable to use plasticizing oils.

Plasticizing oils are understood here as denoting the mineral or vegetable oils commonly employed by those skilled in the art for plasticizing the block copolymers of the styrene/olefin/styrene type used in the composition of the adhesive matrices employed in hydrocolloid adhesive masses.

The mineral oils generally used are mixtures of compounds of a paraffinic, naphthenic or aromatic nature in variable proportions.

Examples of plasticizing oils which may thus be mentioned are the products marketed by SHELL under the names ONDINA® and RISELLA® in the case of mixtures based on naphthenic and paraffinic compounds, or under the name CATENEX® in the case of mixtures based on naphthenic, aromatic and paraffinic compounds.

The mineral plasticizing oil marketed under the name ONDINA® 68 will be particularly preferred within the framework of the present invention.

Within the framework of the production of the hydrocolloid adhesive masses according to the invention, hydrocolloids are understood here as meaning the compounds commonly used by those skilled in the art which are known for their ability to absorb hydrophilic liquids, particularly water, and transport them rapidly. Examples of appropriate hydrocolloids which may be mentioned are polyvinyl alcohol, gelatin, pectin, sodium alginates, natural vegetable gums such as carob gum, karaya gum, guar gum, gum arabic, etc., and cellulose derivatives such as hydroxyethyl celluloses, hydroxypropyl celluloses, carboxymethyl celluloses and their alkali metal salts such as the sodium or calcium salts. These hydrocolloids may be used by themselves or in association.

The alkali metal salts of carboxymethyl cellulose, particularly sodium carboxymethyl cellulose, will be preferred within the framework of the present invention.

In one currently preferred embodiment, the hydrocolloid adhesive mass also contains an acrylate polymer with a glass transition temperature (Tg) below −20° C.

Such acrylate compounds are copolymers formed of:
either at least one monomer selected from the group consisting of acrylic acid alkyl esters in which the linear or branched alkyl group of the ester contains 1 to 18 carbon atoms, preferably 4 to 10 carbon atoms and particularly 4 to 8 carbon atoms, for example methyl, ethyl, n-propyl, n-butyl, isobutyl, n-hexyl, 2-ethylhexyl, n-octyl, isooctyl, n-decyl and n-dodecyl acrylates, associated with acrylic acid;

or at least one monomer selected from the group consisting of acrylic acid alkyl esters in which the linear or branched alkyl group of the ester contains 1 to 18 carbon atoms, preferably 4 to 10 carbon atoms and particularly 4 to 8 carbon atoms, for example methyl, ethyl, n-propyl, n-butyl, isobutyl, n-hexyl, 2-ethylhexyl, n-octyl, isooctyl, n-decyl and n-dodecyl acrylates.

The respective percentages or proportions of these different monomers are adjusted to give a copolymer with the desired glass transition temperature, i.e. below −20° C.

A copolymer containing at least one monomer selected from n-butyl acrylate, 2-ethylhexyl acrylate and isooctyl acrylate, copolymerized with acrylic acid, will preferably be used within the framework of the present invention.

Copolymers containing from 1 to 20% and preferably 1 to 10% by weight of acrylic acid, expressed relative to the total weight of all the monomers, will be very particularly preferred.

Such acrylate compounds can also be homopolymers whose constituent monomer is selected from the group consisting of acrylic acid alkyl esters in which the alkyl group of the ester is either a linear alkyl group containing 2 to 12 carbon atoms or an isobutyl, 2-ethylhexyl or isooctyl group.

Among these homopolymers, poly-n-butyl acrylate will be preferred within the framework of the present invention.

According to one particular characteristic of the invention, the products well known to those skilled in the art for their use in a solventless coating process, known as a hot melt process, will be chosen.

Examples which may thus be mentioned are the products marketed by BASF under the following names:

ACRONAL® A150F (n-butyl acrylate homopolymer with a glass transition temperature of −41° C.), ACRONAL® DS3429 (n-butyl acrylate/2-ethylhexyl acrylate/acrylic acid copolymer with a glass transition temperature of −31° C.), and ACRONAL® DS3458 (n-butyl acrylate/acrylic acid copolymer with a glass transition temperature of −39° C.).

The product marketed by MONSANTO under the name MODAFLOW® (ethyl acrylate/2-ethylhexyl acrylate copolymer) may also be mentioned.

The acrylate polymer marketed under the name ACRONAL® DS3458 will be very particularly preferred within the framework of the present invention.

In one particularly preferred embodiment of the present invention, for adhesive matrices based solely on poly(styrene/olefin/styrene) block copolymers, a hydrocolloid adhesive mass is recommended which comprises:

a) 10 to 35 parts by weight of a poly(styrene/isoprene/styrene) three-block copolymer;
b) 20 to 50 parts by weight of a tackifying resin;
c) 0.5 to 15 parts by weight of an acrylate polymer with a glass transition temperature below −20° C.;
d) 2 to 25 parts by weight of a plasticizing oil;
e) 20 to 50 parts by weight of a hydrocolloid;
f) 0.1 to 2 parts by weight of at least one antioxidant; and
g) 0.2 to 5 parts by weight of ethoxylated sorbitan monooleate.

In another preferred embodiment, this hydrophilic adhesive mass comprises, for a total of 100 parts by weight:

a) 18 to 22 and preferably 17.7 parts by weight of a poly(styrene/isoprene/styrene) three-block copolymer;
b) 20 to 35 and preferably 26.5 parts by weight of a tackifying resin;
c) 3 to 8 and preferably 6.5 parts by weight of an n-butyl acrylate/acrylic acid copolymer with a glass, transition temperature of −39° C.;
d) 10 to 20 and preferably 12.4 parts by weight of a mineral plasticizing oil;
e) 25 to 40 and preferably 35.7 parts by weight of sodium carboxymethyl cellulose;
f) 0.3 to 0.8 and preferably 0.75 part by weight of a phenolic antioxidant and 0.3 to 0.8 and preferably 0.35 part by weight of the sulfur-containing antioxidant zinc dibutyldithiocarbamate; and
g) 0.2 to 3 and preferably 0.5 part by weight of polysorbate 80.

Likewise, in one particularly preferred embodiment of the invention, for adhesive matrices based on polyisobutylene, a hydrocolloid adhesive mass is recommended which comprises:

a) 5 to 20 parts by weight of a (styrene/isoprene/styrene) copolymer;
b) 25 to 50 parts by weight of a low-molecular polyisobutylene;
c) 2 to 20 parts by weight of a polybutene;
d) 20 to 50 parts by weight of a hydrocolloid;
e) 0.2 to 5 parts by weight of an ethoxylated sorbitan monooleate;
f) 0.5 to 15 parts by weight of an acrylate polymer with a glass transition temperature below −20° C.; and
g) 0.1 to 2 parts by weight of at least one antioxidant.

The hydrocolloid adhesive mass according to the invention is useful for medical purposes in any application in which it is necessary to absorb fluids or liquids as from the first few hours. Thus there may be mentioned the production of dressings and bandages for the treatment of blisters, superficial, deep, chronic or acute dermo-epidermal lesions, exudative wounds and burns, and the production of adhesive joints employed in ostomy.

Within the framework of these applications, various products of a dermatological, cosmetological or therapeutic nature can be added to the formulation of the hydrocolloid adhesive mass, examples being antifungals, antimicrobials or antibacterials such as sulfadiazine silver, pH regulators, healing accelerators, vitamins, plant extracts, trace elements, local anesthetics, odor traps, menthol, methyl salicylate, hormones, antiinflammatories, etc.

Within the framework of the production of a dressing for the treatment of blisters or the treatment or protection of wounds, different categories of dermo-epidermal lesions, burns and bedsores, the hydrocolloid adhesive mass according to the invention is coated onto an appropriate support in the desired weight per unit area, according to the techniques known to those skilled in the art, by means of a solvent phase process or, preferably, by means of a hot melt process, or solventless process, at a temperature of between 110 and 160° C.

The support is chosen as a function of the properties required (leaktightness, elasticity, etc.), depending on the type of dressing and the intended application.

It can take the form of a film with a thickness varying from 5 to 150 μm, or a nonwoven or a foam with a thickness of 10 to 500 μm. These supports based on synthetic or natural materials are the ones generally used by those skilled in the art in the field of dressings and the above-mentioned medical applications.

Thus there may be mentioned foams made of polyethylene, polyurethane or PVC, and nonwovens made of polypropylene, polyamide, polyester, ethyl cellulose, etc. It will be preferable, however, to use films as supports, especially polyurethane films, low density polyethylene films, for example those marketed by SOPAL, films based on thermoplastic polyether/polyester copolymer, for example the products marketed under the trade mark Hytrel® by DUPONT DE NEMOURS, or composites based on polyurethane and a nonwoven.

Polyurethane films such as the products marketed by Smith and Nephew under the reference LASSO, or polyurethane films produced from the polyurethane marketed under the name UCECOAT® by UCB or under the name ESTANE® by B.F. GOODRICH, will be preferred within the framework of the present invention.

The dressings produced from the hydrocolloid adhesive mass according to the invention can have any geometric shape, i.e. square, rectangular, circular or oval. Likewise, they can be of any size, according to the surface area of the part to be treated or protected.

In practical terms, the surface of the adhesive mass which is not bonded to the support may be covered with a protective layer or film to be peeled off before the dressing is used. The assembly formed in this way may itself be packaged in a leaktight protection, for example made of polyethylene/ aluminum composites, or in blister packs.

The advantages, characteristics and applications of the invention will be understood more clearly from the following description of Examples and comparative tests.

Of course, these data as a whole do not in any way imply a limitation but are given by way of illustration.

The following abbreviations have been used hereafter for the sake of convenience:

SIS: poly(styrene/isoprene/styrene) three-block copolymer

EXAMPLE 1

12.4 kg of ONDINA® 68 (mineral oil marketed by SHELL), 17.7 kg of VECTOR® 4114 (SIS copolymer marketed by DEXCO), 0.35 kg of PERKACIT® ZDBC (zinc dibutyldithiocarbamate, antioxidant marketed by AKZO) and 0.4 kg of IRGANOX® 1010 (antioxidant marketed by CIBA-GEIGY) are introduced successively into a Z-blade mixer at a temperature of the order of 130° C. The mixture obtained is mixed at between 120 and 140° C. for about 30 minutes. 6.5 kg of ACRONAL® DS3458 (butyl acrylate/acrylic acid copolymer marketed by BASF) are then added and the mixture obtained is mixed for 10 minutes, still at around 130° C. 26.5 kg of WINGTACK® 86 (tackifying resin marketed by GOOD YEAR) are then added and the mixture is mixed for 20 minutes, still at around 130° C. 0.45 kg of MONTANOX® 80VG (polysorbate 80) is then introduced and the mixture is mixed for a further 15 minutes at around 130° C. Finally, 35.7 kg of BLANOSE® 7H4XF (sodium carboxymethyl cellulose marketed by AQUALON) are introduced and the mixture is mixed for a further 30 minutes, still at around 130° C.

The resulting mixture is coated onto a film of siliconized paper at a rate of 1000 g/m$^2$ at a temperature of between 120 and 160° C. The coating produced in this way is transferred to a 30 μm thick, polyurethane final support (produced from the polyurethane marketed under the name UCECOAT® by UCB). Shapes of the appropriate dimensions are then cut out and packaged in heat-sealing sachets or in blister packs.

EXAMPLE 2

The procedure is analogous to that of Example 1 except that in this case a sodium carboxymethyl cellulose of different particle size distribution is used. The 35.7 kg of BLANOSE® 7H4XF are therefore replaced here with the same amount of BLANOSE® 7H3XF (product marketed by AQUALON). Also in this Example, the product is coated onto a film of siliconized paper at a rate of 600 g/m$^2$.

EXAMPLE 3

The procedure is analogous to that of Example 1 except that in this case another sodium carboxymethyl cellulose with different absorption properties is used. The 35.7 kg of BLANOSE® 7H4XF are therefore replaced here with the same amount of AQUASORB® A500 (product marketed by AQUALON). Also in this Example, the product is coated onto a film of siliconized paper at a rate of 400 g/m$^2$.

EXAMPLE 4

13.8 kg of ONDINA® 68, 19.7 kg of VECTOR® 4114, 0.4 kg of PERKACIT® ZDBC and 0.4 kg of IRGANOX® 1010 are introduced successively into a Z-blade mixer at a temperature of the order of 130° C. The mixture obtained is mixed for about 30 minutes, still at around 130° C. 29.5 kg of WINGTACK® 86 are then added and the mixture is mixed for 20 minutes, still at around 130° C. 0.5 kg of MONTANOX® 80VG is then introduced and the mixture is mixed for a further 15 minutes at around 130° C. Finally, 35.7 kg of AQUASORB® A500 are introduced and the mixture is mixed for a further 30 minutes, still at around 130° C. The resulting mixture is coated onto a film of siliconized paper at a rate of 1000 g/m$^2$ at a temperature of between 120 and 160° C. The coating produced in this way is transferred to a 30 μm thick, polyurethane final support (produced from the polyurethane marketed under the name UCECOAT® by UCB). Shapes of the appropriate dimensions are then cut out and packaged in heat-sealing sachets or in blister packs.

EXAMPLE 5

The procedure is analogous to that of Example 4 except that in this case another sodium carboxymethyl cellulose is used. The 35.7 kg of AQUASORB® A500 are therefore replaced here with the same amount of BLANOSE® 7H4XF. Also in this Example, the product is coated onto a film of siliconized paper at a rate of 600 g/m$^2$.

EXAMPLE 6

The procedure is analogous to that of Example 5 except that in this case a sodium carboxymethyl cellulose of different particle size distribution is used. The 35.7 g of BLANOSE® 7H4XF are therefore replaced here with the same amount of BLANOSE® 7H3XF. Also in this Example, the product is coated onto a film of siliconized paper at a rate of 400 g/m$^2$.

EXAMPLE 7

15.3 kg of VECTOR® 4113 (SIS copolymer marketed by DEXCO), 39.4 kg of VISTANEX® LM-MH (low-molecular PIB polymer marketed by EXXON CHEMICAL), 0.2 kg of IRGANOX® 1010 and 8.1 kg of NAPVIS® 10 (polybutene marketed by BP CHEMICALS) are introduced successively into a Z-blade mixer at a temperature of the order of 130° C. The mixture obtained is mixed at around 140° C. for about 40 minutes. 6.5 kg of ACRONAL® DS3458 are then added and the mixture obtained is mixed for about 10 minutes, still at around 140° C. 0.5 kg of MONTANOX® 80VG is then added the mixture is mixed for 10 minutes, still at around 140° C. Finally, 30 kg of BLANOSE® 7H4XF are introduced and the mixture is mixed at around 140° C. for about a further 20 minutes.

The resulting mixture is coated onto a film of siliconized paper at a rate of 1000 g/m$^2$ at a temperature of between 120 and 160° C. The coating produced in this way is transferred to a 30 μm thick, polyurethane final support (produced from the polyurethane marketed under the name UCECOAT® by UCB). Shapes of the appropriate dimensions are then cut out and packaged in heat-sealing sachets or in blister packs.

EXAMPLE 8

13.8 kg of ONDINA® 68, 15.8 kg of VECTOR® 4114, 3.9 kg of VISTANEX® LM-MH, 0.4 kg of PERKACIT® ZDBC and 0.4 kg of IRGANOX® 1010 are introduced successively into a Z-blade mixer at a temperature of the order of 140° C. The mixture obtained is mixed at around 140° C. for about 30 minutes. 29.5 kg of WINGTACK® 86 are then introduced and the mixture is mixed for about a further 35 minutes, still at around 140° C. 0.5 kg of MONTANOX® 65 (polysorbate 65) is then added and the mixture is mixed at 140° C. for about 40 minutes. Finally, 35.7 kg of BLANOSE® 7H4XF are introduced and the mixture is mixed at around 140° C. for about 45 minutes. The resulting mixture is coated onto a film of siliconized paper at a rate of 1000 g/m$^2$ at a temperature of between 120 and 160° C. The coating produced in this way is transferred to a 30 μm thick, polyurethane final support (produced from the polyurethane marketed under the name UCECOAT® by UCB). Shapes of the appropriate dimensions are then cut out and packaged in heat-sealing sachets or in blister packs.

EXAMPLE 9

The procedure is analogous to that of Example 1 except in this case 0.35 kg of IRGANOX® 1010 and 0.5 kg of another ethoxylated sorbitan ester, namely MONTANOX® 65 (polysorbate 65), are used.

EXAMPLE 10

The procedure is analogous to that of Example 9 except that in this case MONTANOX® 60 (polysorbate 60) is used.

EXAMPLE 11

The procedure, is analogous to that of Example 9 except that in this case TWEEN® 81 (polysorbate 81) is used.

EXAMPLE 12

The procedure is analogous to that of Example 1 except that in this case 14.1 kg of CATENEX® N945 (mineral oil marketed by SHELL), 19.6 kg of VECTOR® 4114, 0.4 kg of PERKACIT® ZDBC, 0.4 kg of IRGANOX® 1010, 4.9 kg of ACRONAL® DS3458, 29.7 kg of WINGTACK® 86, 1 kg of MONTANOX® 80VG and 30 kg of BLANOSE® 7H4XF are used. Coating is carried out in the same manner at a rate of 6000 g/m$^2$ and the coating produced in this way is transferred to a 30 μm thick, polyurethane final support marketed under the name LASSO 687 by Smith and Nephew.

EXAMPLE 13

The procedure is identical to that of Example 12 except that in this case the same amount, 1 kg, of another ethoxylated sorbitan ester, namely MONTANOX® 65 (polysorbate 65), is used.

EXAMPLE 14

The procedure is identical to that of Example 1 except that in this case a smaller amount, 0.1 kg, of MONTANOX® 80VG is used. 12.4 kg of ONDINA® 68, 17.8 kg of VECTOR® 4114, 0.35 kg of PERKACIT® ZDBC, 0.35 kg of IRGANOX® 1010, 6.6 kg of ACRONAL® DS3458, 26.6 kg of WINGTACK® 86, 0.1 kg of MONTANOX® 80VG and 35.8 kg of BLANOSE® 7H4XF are therefore used.

COMPARATIVE EXAMPLE 1

12.5 kg of ONDINA® 68, 17.8 kg of VECTOR® 4114, 0.35 kg of PERKACIT® ZDBC and 0.35 kg of IRGANOX® 1010 are introduced successively into a Z-blade mixer at a temperature of the order of 130° C. The mixture obtained is mixed at 130° C. for 35 minutes. 6.5 kg of ACRONAL® DS3458 are then added and the mixture obtained is mixed for 10 minutes, still at 130° C. 26.7 kg of WINGTACK® 86 are then introduced and the mixture is mixed for a further 20 minutes, still at 130° C. Finally, 35.7 kg of BLANOSE® 7H4XF are introduced and the mixture is mixed for a further 25 minutes. The resulting mixture is coated onto a film of siliconized paper at a rate of 1000 g/m$^2$ at a temperature of between 120 and 160° C. The coating produced in this way is transferred to a 30 μm thick, polyurethane final support (produced from the polyurethane marketed under the name UCECOAT® by UCB). Shapes of the appropriate dimensions are then cut out and packaged in heat-sealing sachets or in blister packs.

COMPARATIVE EXAMPLE 2

The procedure is analogous to that of Comparative Example 1 except that in this case a sodium carboxymethyl cellulose of different particle size distribution is used. The 35.7 kg of BLANOSE® 7H4XF are therefore replaced here with the same amount of BLANOSE® 7H3XF. Also in this Example, the product is coated onto a film of siliconized paper at a rate of 600 g/m$^2$.

COMPARATIVE EXAMPLE 3

The procedure is analogous to that of Comparative Example 1 except that in this case another sodium carboxymethyl cellulose with different absorption properties is used. The 35.7 kg of BLANOSE® 7H4XF are therefore replaced here with the same amount of AQUASORB® A500. Also in this Example, the product is coated onto a film of siliconized paper at a rate of 400 g/m$^2$.

COMPARATIVE EXAMPLE 4

13.9 kg of ONDINA® 68, 19.8 kg of VECTOR® 4114, 0.4 kg of PERKACIT® ZDBC and 0.4 kg of IRGANOX® 1010 are introduced successively into a Z-blade mixer at a temperature of the order of 130° C. The mixture obtained is mixed at 130° C. for 35 minutes. 29.8 kg of WINGTACK® 86 are then introduced and the mixture is mixed for a further 20 minutes, still at 130° C. Finally, 35.7 kg of AQUASORB® A500 are added and the mixture is mixed for a further 25 minutes. The resulting mixture is coated onto a film of siliconized paper at a rate of 1000 g/m$^2$ at a temperature of between 120 and 160° C. The coating produced in this way is transferred to a 30 µm thick, final support based on UCECOAT® polyurethane, which is identical to that of Example 4. Shapes of the appropriate dimensions are then cut out and packaged in heat-sealing sachets or in blister packs.

COMPARATIVE EXAMPLE 5

The procedure is analogous to that of Comparative Example 4 except that in this case another sodium carboxymethyl cellulose is employed. The AQUASORB® A500 is replaced with the same amount of BLANOSE® 7H4XF. The product is coated at a rate of 600 g/m² in this case.

COMPARATIVE EXAMPLE 6

The procedure is analogous to that of Comparative Example 5 except that in this case a sodium carboxymethyl cellulose of different particle size distribution is employed. The BLANOSE® 7H4XF is replaced with the same amount of BLANOSE® 7H3XF. Also, the product is coated at a rate of 400 g/m² in this case.

COMPARATIVE EXAMPLE 7

15.4 kg of VECTOR® 4113, 39.7 kg of VISTANEX® LM-MH, 0.2 kg of IRGANOX® 1010 and 8.2 kg of NAPVIS® 10 are introduced successively into a Z-blade mixer at a temperature of the order of 130° C. and the mixture obtained is mixed at around 140° C. for about 40 minutes. 6.5 kg of ACRONAL® DS3458 are then added and the mixture obtained is mixed for about 10 minutes, still at around 140° C. Finally, 30 kg of BLANOSE® 7H4XF are introduced and the mixture is mixed at around 140° C. for about a further 20 minutes. The resulting mixture is coated onto a film of siliconized paper at a rate of 1000 g/m² at a temperature of between 120 and 160° C. The coating produced in this way is transferred to a 30 µm thick, polyurethane final support (produced from the polyurethane marketed under the name UCECOAT® by UCB). Shapes of the appropriate dimensions are then cut out and packaged in heat-sealing sachets or in blister packs.

COMPARATIVE EXAMPLE 8

13.95 kg of ONDINA® 68, 15.8 kg of VECTOR® 4114, 3.95 kg of VISTANEX® LM-MH, 0.4 kg of PERKACIT® ZDBC and 0.4 kg of IRGANOX® 1010 are introduced successively into a Z-blade mixer at a temperature of the order of 140° C. The mixture obtained is mixed at around 140° C. for about 30 minutes. 29.8 kg of WINGTACK® 86 are then introduced and the mixture is mixed for about a further 35 minutes, still at 140° C. Finally, 35.7 kg of BLANOSE® 7H4XF are introduced and the mixture is mixed at around 140° C. for a further 45 minutes. The resulting mixture is coated onto a film of siliconized paper at a rate of 1000 g/m² at a temperature of between 120 and 160° C. The coating produced in this way is transferred to a 30 µm thick, polyurethane final support (produced from the polyurethane marketed under the name UCECOAT® by UCB). Shapes of the appropriate dimensions are then cut out and packaged in heat-sealing sachets or in blister packs.

COMPARATIVE EXAMPLE 9

The procedure is analogous to that of Comparative Example 1 except that in this case different amounts of BLANOSE® 7H4XF and ACRONAL® DS3458 in particular, another mineral oil, namely CATENEX® N945, and another support are used. 14.3 kg of CATENEX® N945, 19.8 kg of VECTOR® 4114, 0.4 kg of PERKACIT® ZDBC, 0.4 kg of IRGANOX® 1010, 4.9 kg of ACRONAL® DS3458, 30.2 kg of WINGTACK® 86 and 30 kg of BLANOSE® 7H4XF are therefore employed. The mixture obtained is coated in the same manner at between 120 and 160° C. onto a film of siliconized paper at a rate of 600 g/m². The coating produced in this way is transferred to a 30 µm thick, polyurethane final support marketed under the name LASSO 687 by Smith and Nephew.

TESTS

To demonstrate the increase in the absorption capacity of the hydrocolloid adhesive masses according to the invention as from the first hour, absorption measurements were made on different samples obtained from Examples 1 to 14 to give the absorption value at one hour, A(EXn), for each Example n.

For comparison purposes, the same procedure was applied to determination of the absorption of hydrocolloid adhesive masses which were identical except that no ethoxylated sorbitan fatty acid ester was incorporated, the samples used corresponding to Comparative Examples 1 to 9, to give the absorption value at one hour, A(CEn), for each Comparative Example n.

These measurements were made according to the following protocol:

The sample used is produced as described in Examples 1 to 14 and Comparative Examples 1 to 9, being formed of the final support, the hydrocolloid adhesive mass and the film of siliconized paper serving as a peel-off protector, which is cut to produce an adhesive tape. The measurement is made using a measuring cell consisting of an aluminum cylinder on which a test sample of adhesive tape is placed and to which a support is subsequently fixed in order to hold the cylinder/sample assembly firmly together. The peripheral part of this support has a siliconized joint to which the peripheral section of the sample sticks when pressed on.

The absorption is measured by the difference in weight of the support/adhesive tape/cylinder assembly before and after the sample has been brought into contact for a fixed period of time, in this case one hour, with a reference liquid.

In the following tests, the reference liquid is a solution of dextran D4876 (marketed by Sigma) containing 60 g per liter in 0.15 molar sodium chloride solution.

The measurements are made according to the following steps:

A sample (e.g. of 16 cm² in this case) of the adhesive tape to be tested is cut out and the protective film is removed.

The sample is incorporated into the measuring cell as described above.

The resulting assembly is weighed; let $P_0$ be the weight obtained.

20 ml of the preprepared reference liquid are then introduced into the cylinder.

The assembly is left in contact with the liquid at 23° C. for 1 hour.

After one hour, the support/sample/cylinder assembly is reweighed after the unabsorbed solution has been removed; let $P_1$ be the weight obtained.

The absorption capacity, corresponding to the surface absorption, is calculated using the following formula: Absorption=$4(P_1-P_0)/\pi D^2$, where D is the diameter of the cylinder, i.e. 0.0357 m in this case.

The absorption, expressed in g/m², is thus defined here by:

Absorption=$(P_1-P_0)10^3$.

Each test is performed at least 5 times.

The absorption capacity obtained is the mean of these different attempts.

These absorption values are used to calculate the difference in absorption between the values of the formulations according to the invention, A(EXn), and the values of the corresponding formulations without ethoxylated sorbitan fatty acid ester, A(CEn). D, expressed as a percentage, represents the increase obtained relative to the sample without ethoxylated sorbitan fatty acid ester.

$$D = \frac{A(EXn) - A(CEn)}{A(CEn)} \times 100$$

The results obtained have been collated in Tables I, II and III.

absorption capacity of the hydrocolloid adhesive masses according to the invention as from the first hour.

Thus it is seen from this Table that there is a substantial difference in the percentage absorption, at one hour, of the hydrocolloid adhesive masses according to the invention compared with hydrocolloid adhesive masses without polysorbate 80, since there is an increase D of the order of 17 to 30%, which even reaches 42% in the case of Example 6.

It is also noted that this increase is found for all the coating weights tested, i.e. 1000, 600 and 400 g/m$^2$.

Likewise, if the: nature of the sodium carboxymethyl cellulose is varied—different particle size distribution between Examples 1, 5, 7 and 8 and Examples 2 and 6, or different absorption capacity of the carboxymethyl cellulose (Examples 3 and 4)—the increase in absorption at one hour is always preserved.

TABLE I

|   | EX1 | CE1 | EX2 | CE2 | EX3 | CE3 | EX4 | CE4 | EX5 | CE5 | EX6 | CE6 | EX7 | CE7 | EX8 | CE8 |
|---|---|---|---|---|---|---|---|---|---|---|---|---|---|---|---|---|
| A | 1760 | 1500 | 1670 | 1270 | 1170 | 1000 | 890 | 690 | 1190 | 950 | 1040 | 730 | 1900 | 1620 | 1250 | 1060 |
| D | 17.3 | | 31 | | 17 | | 29 | | 25.2 | | 42.5 | | 17.3 | | 18 | |
| G | 1000 | | 600 | | 400 | | 1000 | | 600 | | 400 | | 1000 | | 1000 | |
| CMC | 7H4XF | | 7H3XF | | A500 | | A500 | | 7H4XF | | 7R3XF | | 7H4XF | | 7H4XF | |

G: represents the coating weight of the adhesive tapes used to measure the absorption, expressed in g/m$^2$.
A: represents the absorption at one hour, expressed in g/m$^2$.
D: represents the difference in absorption at one hour between the Examples, A(EXn), and the Comparative Examples, A(CEn), relative to the absorption of the corresponding Comparative Example, A(CEn), expressed as a percentage.

TABLE II

Use of different ethoxylated sorbitan esters

|   | CE1 | EX1 | EX9 | EX10 | EX11 |
|---|---|---|---|---|---|
| A | 1500 | 1760 | 1760 | 1710 | 1810 |
| D |  | 17.3 | 17.3 | 14 | 20.6 |

D: represents the difference in absorption at one hour between the Examples, A(EXn), and the Comparative Example, A(CE1), relative to the absorption of the Comparative Example, A(CE1), expressed as a percentage.
A: represents the absorption at one hour, expressed in g/m$^2$.
All the adhesive tapes used have a coating weight of 1000 g/m$^2$ on a polyurethane support.

TABLE III

Use of different concentrations of ethoxylated sorbitan esters

|   | CE1 | EX14 | CE9 | EX12 | CE9 | EX13 |
|---|---|---|---|---|---|---|
| A | 1500 | 1710 | 630 | 870 | 630 | 890 |
| D |  | 14 |  | 38 |  | 41.2 |
| CMC | 35.7 | 35.7 | 30 | 30 | 30 | 30 |
| G | 1000 | 1000 | 600 | 600 | 600 | 600 |

CMC: represents the proportion of BLANOSE ® 7H4XF present in the hydrocolloid adhesive mass, expressed as a percentage.
G: represents the coating weight of the adhesive tapes used to measure the absorption, expressed in g/m$^2$.
A: represents the absorption at one hour, expressed in g/m$^2$.
D: represents the difference in absorption at one hour between the Example, A(EXn), and the Comparative Example, A(CEn), relative to the absorption of the Comparative Example, A(CEn), expressed as a percentage.
All the adhesive tapes used are on a 30 μm thick polyurethane support.

Analysis of the results collated in Table I gives a perfect illustration of the favorable action of polysorbate 80 or polysorbate 65, in the case of Example 8, on the increase in An increase in absorption for different proportions of carboxymethyl cellulose in the hydrocolloid adhesive mass is also found, being 35.7% in Examples 1 to 6 and 8 and 30% in Example 7.

This phenomenon is also found whatever the nature of the hydrocolloid adhesive mass. Thus the results are comparable, whatever the sodium carboxymethyl cellulose used or the coating weight obtained, for a hydrocolloid adhesive mass composed of poly(styrene/isoprene/styrene) copolymer, tackifying resin and plasticizer, either with (Examples 1, 2 and 3) or without (Examples 4, 5, 6 and 8) an acrylate copolymer with a glass transition temperature below −20° C., so the absence of this compound does not modify the results or the increase in absorption capacity as from the first hour, due to the ethoxylated sorbitan ester.

Likewise, identical results are found with an adhesive matrix based on low-molecular polyisobutylene and poly(styrene/isoprene/styrene) block copolymer. Thus, in Example 7, where the adhesive matrix comprises 39.4% of poly-isobutylene, 15.3% of p6oly(styrene/isoprene/styrene) block copolymer and 8.1% of polybutylene, there is an increase in absorption capacity of 17.3% as from the first hour, compared with an identical hydrocolloid adhesive mass without polysorbate 80.

Similarly, an analogous result is obtained in Example 8 with a different kind of adhesive matrix based on 3.95% of polyisobutylene and 15.8% of poly(styrene/isoprene/styrene) block copolymer, without polyisobutylene but with a mineral oil.

Analysis of the results collated in Table II illustrates the favorable action of various ethoxylated sorbitan esters on the increase in absorption capacity, as from the first hour, of the hydrocolloid adhesive masses according to the invention.

It is also seen from this Table that this increase is of the order of 15 to 20% whatever the nature of the ester used (stearate in the case of polysorbates 60 and 65 or oleate in the case of polysorbates 80 and 81), the number of ethoxylated units w+x+y=z used (5 in the case of polysorbate 81 and 20 in the case of polysorbates 65, 60 and 80) and the number of esters present (monoester in the case of polysorbate 60 and triesters in the case of polysorbate 65).

The results collated in Table III illustrate the action of different concentrations of ethoxylated sorbitan esters on the increase in absorption at 1 hour. Thus it can be noted that polysorbate 65 (Example 13) and polysorbate 80 (Example 12), used with a smaller proportion of carboxymethyl cellulose than in Table II (30% instead of 35.7%) and present in this case in a proportion of 1% instead of the 0.5% in Table II, effects a significant increase in absorption of the order of 40%, relative to a product without polysorbate (Comparative Example 9).

Example 14, which contains only 0.1% of polysorbate 80, shows a 14% increase in absorption capacity. Once again, positive results are found irrespective of the coating weight (1000 g/m² in Example 14 and 600 g/m² in Examples 12 and 13).

It is also seen from these results that polysorbates are capable of increasing the absorption capacity as from the first hour in very small proportions, being effective at 0.5% in Examples 1 to 11 and even at 0.1% in Example 14. This is an essential factor in the production of an ideal dressing without degrading the physical properties (adhesion, cohesion, integrity, elasticity).

The compatibility problems which can arise with the other compounds of the hydrocolloid adhesive mass are thus avoided, so it is easy to obtain a homogeneous product which has the correct appearance and is stable over time.

Another appreciable advantage of these polysorbates is that these compounds are already used in numerous industrial sectors, such as pharmacy, cosmetics or human and animal nutrition, in which their safety, stability, biodegradability and lack of ecotoxicity have been demonstrated.

Their use in the production of dressings therefore presents no problems of pharmaceutical validation because they do not exhibit any particular danger.

In conclusion, all these findings and remarks undeniably show that the addition of ethoxylated sorbitan esters, such as polysorbate 80, makes it possible to increase the absorption capacity of the hydrocolloid adhesive masses as from the first few hours, and demonstrate the resulting positive consequences for the production of dressings for the treatment of wounds, bedsores, burns and superficial, chronic, deep or acute dermo-epidermal lesions.

What is claimed is:

1. An absorptive blister, lesion, burn, or wound dressing containing a hydrocolloid adhesive mass for medical purposes, which comprises:
   a) 0.2 to 5 parts by weight of an ethoxylated sorbitan fatty acid ester;
   b) 20 to 50 parts by weight of a hydrocolloid;
   c) 32 to 120 parts by weight of an adhesive matrix made up of one or more polymers selected from the group consisting of poly(styrene/olefin/styrene) block copolymers, low-molecular polyisobutylenes and high-molecular polyisobutylenes, and one or more compounds selected from the group consisting of tackifying resins, plasticizers, polybutenes, antioxidants, ethylene/vinyl acetate copolymers, butyl rubbers and ethylene/propylene block copolymers; and
   d) 0 to 15 parts by weight of an acrylate polymer with a glass transition temperature below −20° C.

2. The absorptive dressing according to claim 1, which comprises:
   a) 0.2 to 5 parts by weight of an ethoxylated sorbitan fatty acid ester;
   b) 20 to 50 parts by weight of a hydrocolloid;
   c) 32 to 120 parts by weight of an adhesive matrix made up of one or more polymers selected from the group consisting of poly(styrene/olefin/styrene) block copolymers, low-molecular polyisobutylenes and high-molecular polyisobutyleries, and one or more compounds selected from the group consisting of tackifying resins, plasticizers, polybutenes, antioxidants, ethylene/vinyl acetate copolymers, butyl rubbers and ethylene/propylene block copolymers; and
   d) 0.5 to 15 parts by weight of an acrylate polymer with a glass transition temperature below −20° C.

3. The absorptive dressing according to claim 1, wherein the ethoxylated sorbitan fatty acid ester is selected from the group consisting of polysorbate 20, polysorbate 21, polysorbate 40, polysorbate 60, polysorbate 61, polysorbate 65, polysorbate 80, polysorbate 81, polysorbate 85 and polysorbate 120.

4. The absorptive dressing according to claim 2, wherein the ethoxylated sorbitan fatty acid ester is selected from the group consisting of polysorbate 20, polysorbate 21, polysorbate 40, polysorbate 60, polysorbate 61, polysorbate 65, polysorbate 80, polysorbate 81, polysorbate 85 and polysorbate 120.

5. The absorptive dressing according to claim 1, wherein the ethoxylated sorbitan fatty acid ester is an ethoxylated sorbitan monoester.

6. The absorptive dressing according to claim 2, wherein the ethoxylated sorbitan fatty acid ester is an ethoxylated sorbitan monoester.

7. The adhesive dressing according to claim 2, wherein the acrylate polymer with a glass transition temperature below −20° C. is a copolymer formed of at least one acrylic acid alkyl ester monomer having an alkyl group that is branched or linear and has 1 to 18 carbon atoms, copolymerized with acrylic acid.

8. The adhesive dressing according to claim 2, wherein the acrylate polymer with a glass transition temperature below −20° C. is a copolymer formed of at least one acrylic acid alkyl ester monomer having an alkyl group that is branched or linear and has 4 to 10 carbon atoms, copolymerized with acrylic acid.

9. The absorptive dressing according to claim 2, wherein the acrylate polymer with a glass transition temperature below −20° C. is a copolymer formed of at least one monomer selected from the group consisting of methyl, ethyl, n-propyl, n-butyl, isobutyl, n-hexyl, 2-ethylhexyl, n-octyl, isooctyl, n-decyl and n-dodecyl acrylates, copolymerized with acrylic acid.

10. The absorptive dressing according to claim 7, wherein the above-mentioned acrylate copolymer is a copolymer formed of at least one monomer selected from the group consisting of n-butyl acrylate, 2-ethylhexyl aprylate and isooctyl acrylate, copolymerized with acrylic acid.

11. The absorptive dressing according to claim 7, wherein the above-mentioned acrylate copolymer is a copolymer selected from the group consisting of an n-butyl acrylate/acrylic acid copolymer with a glass transition temperature of −39° C. and an n-butyl acrylate/2-ethylhexyl acrylate/acrylic acid copolymer with a glass transition temperature of −31° C.

12. The absorptive dressing according to claim 10, wherein the above-mentioned acrylate copolymer comprises from 1 to 20% by weight of acrylic acid, expressed relative to the total weight of all the monomers.

13. The absorptive dressing according to claim 10, wherein the above-mentioned acrylate copolymer comprises from 1 to 10% by weight of acrylic acid, expressed relative to the total weight of all the monomers.

14. The adhesive dressing according to claim 2, wherein the acrylate polymer with a glass transition temperature below −20° C. is a copolymer formed of at least two acrylic acid alkyl ester monomers each having an alkyl group that is branched or linear and has 1 to 18 carbon atoms, copolymerized with acrylic acid.

15. The adhesive dressing according to claim 2, wherein the acrylate polymer with a glass transition temperature below −20° C. is a copolymer formed of at least two monomers acrylic acid alkyl ester monomers each having an alkyl group that is branched or linear and has 4 to 10 carbon atoms, copolymerized with acrylic acid.

16. The absorptive dressing according to claim 2, wherein the acrylate polymer with a glass transition temperature below −20° C. is a copolymer formed of at least two monomers selected from the group consisting of methyl, ethyl, n-propyl, n-butyl, isobutyl, n-hexyl, 2-ethylhexyl, n-octyl, isooctyl, n-decyl and n-dodecyl acrylates.

17. The adhesive dressing according to claim 2, wherein the acrylate polymer with a glass transition temperature below −20° C. is a homopolymer whose constituent monomer is an acrylic acid alkyl ester monomer selected from the group consisting of a linear alkyl group that has 2 to 12 carbon atoms, an isobutyl group, a 2-ethylhexyl group and a isooctyl group.

18. The absorptive dressing according to claim 17, wherein said acrylate polymer is an n-butyl acrylate homopolymer with a glass transition temperature of −41° C.

19. An absorptive blister, lesion, burn, or wound dressing containing a hydrocolloid adhesive mass comprising:
   a) 0.2 to 5 parts by weight of an ethoxylated sorbitan fatty acid ester;
   b) 20 to 50 parts by weight of a hydrocolloid; and
   c) 32 to 120 parts by weight of an adhesive matrix made up of one or more polymers selected from the group consisting of poly(styrene/olefin/styrene) block copolymers, low-molecular polyisobutylenes and high-molecular polyisobutylenes, and one or more compounds selected from the group consisting of tackifying resins, plasticizers, polybutenes, antioxidants, ethylene/vinyl acetate copolymers, butyl rubbers and ethylene/propylene block copolymers.

20. The absorptive dressing according to claim 1, wherein the adhesive matrix of said hydrocolloid adhesive mass consists of:
   10 to 35 parts by weight of a poly(styrene/olefin/styrene) block copolymer;
   2 to 25 parts by weight of a plasticizer;
   0.1 to 2 parts by weight of at least one antioxidant; and
   20 to 50 parts by weight of a tackifying resin.

21. The absorptive dressing according to claims 1, wherein the adhesive matrix of said hydrocolloid adhesive mass consists of:
   10 to 35 parts by weight of a poly(styrene/isoprene/styrene);
   2 to 25 parts by weight of a plasticizing oil;
   0.1 to 2 parts by weight of at least one antioxidant; and
   20 to 50 parts by weight of a tackifying resin.

22. The absorptive dressing according to claim 20, wherein the above-mentioned plasticizer is a mineral plasticizing oil selected from the group consisting of naphthenic, paraffinic and aromatic compounds.

23. The absorptive dressing according to claim 1, wherein the adhesive matrix of said hydrocolloid adhesive mass comprises one or more polyisobutylenes with a low molecular weight of between 40,000 and 80,000 daltons.

24. The absorptive dressing according to claim 1, wherein the adhesive matrix of said hydrocolloid adhesive mass comprises at least one low-molecular polyisobutylene and at least one compound selected from the group consisting of high-molecular polyisobutylenes, polybutenes, butyl rubbers, ethylene/vinyl acetate copolymers, ethylene/propylene block copolymers poly(styrene/isoprene/styrene) block copolymers and poly (styrene/butadiene/styrene) block copolymers.

25. The absorptive dressing according to claim 24, wherein the adhesive matrix of said hydrocolloid adhesive mass comprises at least one low-molecular polyisobutylene and at least one compound selected from the; group consisting of polybutenes, butyl rubbers and high-molecular polyisobutylenes.

26. The absorptive dressing according to claim 23, wherein the adhesive matrix of said hyrocolloid adhesive mass comprises at least one low-molecular polyisobutylene, one poly(styrene/olefin/styrene) block copolymer and one polybutene.

27. The absorptive dressing according to claim 26, which comprises:
   a) 5 to 20 parts by, weight of a poly(styrene/isoprene/styrene) block copolymer;
   b) 25 to 50 parts by weight of at least one low-molecular polyisobutylene;
   c) 2 to 20 parts by weight of a polybutene;
   d) 20 to 50 parts by weight of a hydrocolloid;
   e) 0.2 to 5 parts by weight of an ethoxylated sorbitan monooleate;
   f) 0.5 to 15 parts by weight of an acrylate polymer with a glass transition temperature below −20° C.; and
   g) 0.1 to 2 parts by weight of at least one antioxidant.

28. The absorptive dressing according to claim 1, which comprises, for a total of 100 parts by weight:
   a) 18 to 22 parts by weight of a poly(styrene/isoprene/styrene) three-block copolymer;
   b) 20 to 35 parts by weight of a tackifying resin;
   c) 3 to 8 parts by weight of an n-butyl acrylate/acrylic acid copolymer with a glass transition temperature of −39° C.;
   d) 10 to 20 parts by weight of a mineral plasticizing oil;
   e) 25 to 40 parts by weight of sodium carboxymethyl cellulose;
   f) 0.3 to 0.8 parts by weight of a phenolic antioxidant and 0.3 to 0.8 parts by weight of the sulfur-containing antioxidant zinc dibutyldithiocarbamate; and
   g) 0.2 to 3 parts by weight of polysorbate 80.

29. The absorptive dressing according to claim 1, which comprises, for a total of 100 parts weight:
   a) 17.7 parts by weight of a poly(styrene/isoprene/styrene) three-block copolymer;
   b) 26.5 parts by weight of a tackifying resin;
   c) 6.5 parts by weight of an n-butyl acrylate/acrylic acid copolymer with a glass transition temperature of −39° C.;
   d) 12.4 parts by Weight of a mineral plasticizing oil;
   e) 35.7 parts by weight of sodium carboxymethyl cellulose;
   f) 0.75 part by weight of a phenolic antioxidant and 0.3 to 0.8 parts by weight of the sulfur- containing antioxidant zinc dibutyldithiocarbamate; and g) 0.5 part by weight of polysorbate 80.

30. The absorptive dressing according to claim 1, wherein the above-mentioned block copolymer is a poly(styrene/isoprene/styrene) with a styrene content of between 14 and 52% by weight, based on the weight of said copolymer.

31. The absorptive dressing according to claim 1, wherein the above-mentioned block copolymer is a poly(styrene/isoprene/styrene) with a styrene content of between 14 and 30% by weight, based on the weight of said copolymer.

32. The absorptive dressing according to claim 1, wherein the hydrocolloid is an alkali metal salt of carboxymethyl cellulose.

33. The absorptive dressing according to claim 1, wherein the hydrocolloid is a sodium carboxymethyl cellulose.

34. A dressing for the treatment of blisters, superficial, deep, chronic or acute dermo-epidermal lesions of the skin, exudative wounds or burns, which dressing comprises a support onto which a hydrocolloid adhesive mass is coated, wherein the hydrocolloid adhesive mass comprises:

a) 0.2 to 5 parts by weight of an ethoxylated sorbitan fatty acid ester;

b) 20 to 50 parts by weight of a hydrocolloid;

c) 32 to 120 parts by weight of an adhesive matrix made up of one or more polymers selected from the group consisting of poly(styrene/olefin/styrene) block copolymers, low-molecular polyisobutylenes and high-molecular polyisobutylenes, and one or morecompounds selected from the group consisting of tackifying resins, plasticizers, polybutenes, antioxidants, ethylene/vinyl acetate copolymers, butyl rubbers and ethylene/propylene block copolymers; and d) 0 to 15 parts by weight of an acrylate polymer with a glass transition temperature below −20° C.

35. A method of treating a skin blister, lesion, burn, or wound, which comprises applying an absorbent dressing to a skin blister, lesion, burn, or wound for a period of time sufficient to absorb an exudate from the blister, lesion, burn, or wound, said absorbent dressing containing a hydrocolloid adhesive mass that comprises:

a) 0.2 to 5 parts by weight of an ethoxylated sorbitan fatty acid ester;

b) 20 to 50 parts by weight of a hydrocolloid; and c) 32 to 120 parts by weight of an adhesive matrix made up of one or more polymers selected from the group consisting of poly(styrene/olefin/styrene) block copolymers, low-molecular polyisobutylenes and high-molecular polyisobutylenes, and one or more compounds selected from the group consisting of tackifying resins, plasticizers, polybutenes, antioxidants, ethylene/vinyl acetate copolymers, butyl rubbers and ethylene/propylene block copolymers, wherein the hydrocolloid is present in an amount of 25 to 40 percent of the hydrocolloid adhesive mass.

* * * * *

UNITED STATES PATENT AND TRADEMARK OFFICE
CERTIFICATE OF CORRECTION

PATENT NO. : 6,375,977 B1
DATED : April 23, 2002
INVENTOR(S) : Stephane Auguste et al.

It is certified that error appears in the above-identified patent and that said Letters Patent is hereby corrected as shown below:

<u>Title page,</u>
Item [73], Assignee, change "Laboratories" to -- Laboratoires --.

<u>Column 2,</u>
Line 26, change "theirate" to -- the rate --.

<u>Column 4,</u>
Line 24, change "bums" to -- burn --.

<u>Column 17,</u>
Line 36, change "lack. of (delete period)" to -- lack of --.
Line 48, change "bum" to -- burn --.

<u>Column 18,</u>
Lines 7 to 8, change "high-molecular polyisobutyleries" to -- high-molecular polyisobutylenes --.

<u>Column 19,</u>
Line 56, change "claims 1" to -- claim 1 --.

<u>Column 21,</u>
Line 17, change "bum" to -- burn --.

Signed and Sealed this

Tenth Day of December, 2002

JAMES E. ROGAN
*Director of the United States Patent and Trademark Office*